| United States Patent [19] | [11] Patent Number: 4,877,612 |
| --- | --- |
| Berger et al. | [45] Date of Patent: Oct. 31, 1989 |

[54] IMMUNOLOGICAL ADJUVANT AND PROCESS FOR PREPARING THE SAME, PHARMACEUTICAL COMPOSITIONS, AND PROCESS

[75] Inventors: Frank M. Berger, 190 E. 72nd St., New York, N.Y. 10021; Constantin Bona, New York, N.Y.; Mary P. Lechevalier, Piscataway, N.J.

[73] Assignee: Frank M. Berger, New York, N.Y.

[21] Appl. No.: 902,378

[22] Filed: Sep. 2, 1986

Related U.S. Application Data

[63] Continuation of Ser. No. 735,904, May 20, 1985, abandoned.

[51] Int. Cl.$^4$ ............................................... A61K 39/02
[52] U.S. Cl. ...................................... 424/92; 514/885; 514/938; 514/942
[58] Field of Search .................. 424/92; 514/885, 938, 514/947

[56] References Cited

U.S. PATENT DOCUMENTS 4,010,257  3/1977  Adlam et al. ......................... 424/92

OTHER PUBLICATIONS

Chem. Abst., 84:111,636r, 1976.

Primary Examiner—John W. Rollins

[57] ABSTRACT

A process is provided for preparing immunological adjuvants (which are unusual in that they do not contain mycolic acids, mycolic acid esters or lipopolysaccharides, and can increase the immune response in animals of soluble and particulate antigens without the presence of oil or oily vehicles, and without inducing adjuvant arthritis or other undesirable side effects) by solvent extraction from a species of Amycolata, a genus of filamentous branching bacteria known as Amycolata, as well as pharmaceutical compositions containing such adjuvants, and a process for increasing the immune response of antigens in animals by administration of such adjuvants.

22 Claims, No Drawings

IMMUNOLOGICAL ADJUVANT AND PROCESS FOR PREPARING THE SAME, PHARMACEUTICAL COMPOSITIONS, AND PROCESS

This is a continuation of application Ser. No. 735,904, filed May 20, 1985, now abandoned.

Adjuvants are substances that are capable of increasing the immune response of a wide variety of chemically unrelated antigens. Antigens are substances foreign to the body which on parenteral administration (by some way other than through the digestive tract) induce the formation of antibodies. Antibodies are substances contained in blood, in other body fluids and tissues that bind the antigen and render it harmless to the body. Antibodies are one of the natural defense mechanisms of the body. When present, they kill or render harmless invading pathogenic bacteria, viruses or protozoa. They also are capable of inactivating or killing cancer cells. All antibodies are highly specific and can kill, bind or render harmless only the antigen that has induced their formation.

Vaccines and immunizations are administered in order to induce the formation of protective antibodies. This is achieved by administration of killed microorganisms, administration of microbial products or of extracts or portions of microorganisms or by the use of attenuated strains that are no longer capable of inducing disease but still can engender the production of protective antibodies. Utilizing these methods, a substantial number of important vaccines have been developed which have eliminated or substantially reduced the occurrence of many diseases that in the past endangered the survival of individuals or populations. Examples of vaccines utilizing attenuated or modified living microorganisms are those for the prevention of small pox, poliomyelitis, yellow fever, measles and rubella. Examples of successful vaccines utilizing killed microorganisms are those for the prevention of typhoid, pertussis (whooping cough), pneumonia and cholera. Examples of vaccines produced from bacterial products are those for the prevention of diphtheria and tetanus.

Recovery from certain infectious diseases such as smallpox, typhoid fever and many others produce long-lasting immunity. It is of interest to note that most of the vaccines that are being used at the present time induce protection from diseases that when acquired induce strong and long-lasting immunity. People who survive the first attack of one of these diseases rarely suffer a second attack. The antigenic components of the microorganisms causing these diseases are highly immunogenic, i.e., generate antibodies that protect the animal from contracting the disease on a subsequent encounter with the specific microorganism.

There is, on the other hand, a large number of diseases against which vaccines have not become available. Attenuated strains of microorganisms that would protect against these diseases could not be obtained because of the tendency of these strains to revert promptly to their pathogenic, i.e., disease-inducing-form. An even more important reason for the absence of vaccines that would protect against these diseases is the low immunogenicity of the microorganisms causing these diseases. People who contract a disease caused by such microorganisms that are weakly antigenic and of low immunogenicity are not protected against subsequent reinfection and disease by the same microorganism. Examples of diseases caused by weakly antigenic microorganisms where one attack of the disease does not protect against subsequent attacks are malaria, gonorrhoea, syphilis and herpes.

It has been realized for a long time that a substance that could increase the ability of non-immunogenic microorganisms and soluble proteins and peptides to induce formation of antibodies would be most valuable and would permit the production of vaccines against diseases where protection cannot be induced at the present time. This idea has been on the minds of investigators for many decades.

The first significant advance in this field was made by Glenny, A. I. et al (*J. Path. Bact.* 29, 31–40, 1926) who showed that absorption of diphtheria toxoid on aluminum phosphate increases the immunological response. Substantial work subsequently carried out with a number of inorganic aluminum and calcium compounds indicated that these can be safely used in humans. Unfortunately, these agents increased the immune response only to diphtheria and tetanus toxoids. They did not work satisfactorily as adjuvants with other vaccines and did not significantly increase the immune response to weak antigens.

The most effective composition used for augmentation of immunogenicity of antigens is Freund's Complete Adjuvant (FCA). FCA contains killed mycobacteria dispersed in a water-in-oil emulsion (Freund, J. *Ann. Rev. Microbiol.* 1: 291–309, 1947). Customarily, the antigen is dissolved or dispersed in water and the aqueous phase emulsified in mineral oil with the help of an emulsifying agent. Freund's Incomplete Adjuvant (FIA) does not contain mycobacteria. In addition to their potent adjuvant action, FCA and FIA also induce many undesirable and toxic effects and for this reason cannot be used in humans and domestic animals.

Many efforts have been made to minimize or eliminate the toxic side effects by refining the ingredients of FCA. Attempts to replace the mineral oil which is responsible for granulomatous reactions and an increase in the occurrence of neoplasms in mice by more readily metabolizable fatty substances were unsuccessful.

It was soon recognized that the potent adjuvant action of FCA depends primarily on the presence of mycobacteria in this preparation. The adjuvant active principle of mycobacteria was isolated by Bekierkunst, A. E. et al. (*Infect. Immun.* 4: 256, 1971) and identified as a diester of mycolic acid. The same substance was also isolated by other investigators and named wax D, cord factor, P3, trehalose diester or trechalose dimycolate (Smith, D. W. et al., *Adv. Tuberc. Res.* 16: 191, 1968; Lederer, E., *J. Medic. Chem.* 23: 819, 1980). However, it soon became apparent that the mycolic acid esters were not only responsible for the immuno-enhancing properties of mycobacteria but also induced most of the undesirable side effects caused by FCA. These include pyrogenicity and induction of adjuvant arthritis and of autoimmune diseases (Retzinger, G. S. et al., *J. Immunol.* 129: 735, 1982).

Several groups of investigators attempted to isolate substances from mycobacteria that were unrelated to mycolic acids and nevertheless capable of replacing mycobacteria in FCA. These studies were successful and led to the isolation of peptidoglycans, also called mureins, mucopeptides or glycopeptides. All these substances consist of a polysaccharide (glycan) linked through muramic acid or similar substitutes D-glucosamine residues to peptides. This work culminated in the identification and synthesis of muramyl dipeptide (MDP). This simple peptidoglycan could substitute for whole mycobacteria in FCA (Adam, A. And Lederer, E., *Medic Res. Rev.* 4: 111, 1984). Unfortunately, it soon became apparent that MDP and other peptidoglycans were pyrogenic and induced adjuvant arthritis which would make their use as adjuvants unpermissible in humans and domestic animals (Nagao and Tanaka, *Infect. Immun.* 28: 624, 1980; Zikek, Z. et al., *Infect. Immun.* 35: 674, 1982; Stewart-Tull, D. E. S., *Ann. Rev. Microbiol.* 34: 311, 1980).

Another group of compounds known to possess excellent adjuvant properties are bacterial lipopolysaccharides (LPS), also known as endotoxins. LPS a component of the cell walls of gram-negative bacteria possesses a wide variety of biological properties. The biological activities of LPS are attributable to lipid A which, like LPS, is pyrogenic and toxic to many biological functions (Berger, F. M. *Advances in Pharmacology* 5: 19, 1967). Detoxification of LPS or lipid A by chemical treatment results in the loss of adjuvant properties. These, however, can be in part restored by addition of trehalose dimycolate and oil (Ribi, E. et al., *Cancer Immunol. Immunother.* 7: 43, 1979).

It has been shown that with the use of some of the existing adjuvants such as FCA, trehalose dimycolte or MDP it is possible to induce in animals the production of protective antibodies against infectious microorganisms that given alone are unable to do so. This was clearly demonstrated by Freund et al. (*Am J. Trop. Med.* 28: 1, 1948) who were able to immunize monkeys against malaria by means of killed parasites given together with FCA. It has since been shown that with the help of FCA and MDP it is possible to immunize animals or induce the production of antibodies against a number of viral, microbial and protozoal infections, such as herpes virus 1 and 2, cytomegalovirus, H. influenza, N. gonorrhoea, trypansomiasis, leishmaniosis and many others that are not immunogenic enough to induce an immune response when given by themselves.

Work carried out up to the present has indicated that the substances active as adjuvants are also responsible for the toxic and undesirable effects that accompany use of these agents. This has been specifically demonstrated with adjuvants containing mycolic acid esters, muramic acid or lipopolysaccharides. As a result of this, it is not possible to administer adjuvants containing any of these substances to humans or domestic animals.

In accordance with the invention, an immunological adjuvant capable of increasing the immune response in animals to antigens and substantially free from mycolic acids, mycolic acid esters and lipopolysaccharides is provided, prepared by an extraction procedure from one or more species of Amycolata, a genus of filamentous branching bacteria known as Actinomycetes. Administration of these immunological adjuvants to animals increases the immune response of antigens without the presence of oil or oily vehicles, and without inducing adjuvant arthritis or other undesirable side effects.

The process for preparing such immunological adjuvants in accordance with the invention comprises (1) suspending Amycolata bacteria cells in aqueous physiological saline solution;

(2) subjecting the Amycolata bacteria cells to extraction with a solvent immiscible with the aqueous saline solution and in which the immunological adjuvant is soluble and/or dispersible;

(3) separating the resulting solvent solution of immunological adjuvant from the bacteria cells and the aqueous saline solution; and (4) recovering the adjuvant, all of the foregoing steps being carried out at a temperature below the temperature at which the immunological adjuvant is inactived.

To assist in dispersing the bacteria cells in the aqueous saline solution, a wetting or emulsifying agent such as an anionic or nonionic surfactant can be added.

Also in accordance with the invention, pharmaceutical compositions are provided, suitably but not necessarily, in dosage unit form, for administration to animals to which an antigen is also administered, to increase the immune response of the antigen, and comprising and immune-response-increasing amount of the immunological adjuvant, prepared by the above-described process, and a pharmaceutically-acceptable nontoxic carrier or diluent therefor.

The invention further provides a process for increasing the immune response of antigens which upon admistration to an animal induce the formation of antibodies, which comprises administering to the animal an immunological adjuvant prepared according to the above-described process. The immunological adjuvant can be administered together with or separately from administration of the antigen.

A preferred embodiment of pharmaceutical composition, also preferably in dosage unit form, comprises the immunological adjuvant and the antigen.

The immunological adjuvants described herein are novel, and are prepared by a new extraction process from a genus of bacteria that do not contain mycolic acid and are known as Amycolata, of which some species are new strains not previously known or described.

Amycolata is the name of a genus of filamentous branching bacteria known as actinomycetes (Order: Actinomycetales). The new strains of Amycolata disclosed herein as well as those previously known share the following characteristics:

1. Taxonomically, most strains of Amycolata which have been previously described were assigned to the genera Streptomyces or Nocardia.

2. Morphologically, amycolatae belong to the "nocardioform" group of actinomycetes. Nocardioform is a broad descriptive term for actinomycetes which form branching filaments that tend to break down into smaller, squarish units as a normal stage of their cycle of growth. In this they are similar to members of the genus Nocardia (Prauser, H., *Publ. Fac. Sci. Univ. Purkyne Brno K*40: 196, 1967).

3. Chemically, Amycolata spp. have a peptidoglycan (cell wall) of chemotype IV (Becker, B. et al., *Appl. Microbiol.* 13: 236, 1965). This is to say that, like nocardiae, the components of the wall include meso diaminopimelic acid, glutamic acid, alanine, glucosamine, muramic acid, arabinose and galactose. Their whole cell sugar pattern is of type A (Lechevalier, M. P., *J. Lab. Clin. Med.* 71: 934, 1968): galactose and arabinose. However, unlike Nocardia spp., the cell lipids contain no mycolic acids (Lechevalier, M. P., *J. Bacteriol.* 105: 313, 1971; Lechevalier, M. P., *Can. J. Microbiol.* 19: 965, 1973), the fatty acids are of the branched-chain and normal types (no major amounts of unsaturated ones are present) and their phospholipids are of the PIII type (phosphatidylcholine as diagnostic constituent) (Lechevalier, M. P., *Biochem. Syst. Ecol.* 5: 249, 1977; Lechevalier, M. P., *Zbl. Bact. Suppl.* 11: 111, 1981). Thus, chemically they differ from members of the genus Nocardia.

4. Physiologically, Amycolatae are very diverse; they can be described as mycolateless nocardiae.

5. Amycolatae have been isolated from many different sources, including air, soil and vegetable matter.

The Amycolata spp. used herein as a source of the immunological adjuvants of the invention conform to the above description: i.e., they are nocardioform actinomycetes with a cell composition of chemotype IV, a whole cell sugar pattern of type A, no mycolates and a phospholipid pattern of type PIII. All occur naturally and were isolated from earth or soil, as indicated below using the following procedure:

Two grams of soil are shaken for 30 minutes at 215 RPM at 28° C. in 100 cc sterile water, then the suspension permitted to settle out for 10 minutes without further shaking. One ml of the supernatant is added to a 9 ml sterile water blank, this mixed thoroughly, then diluted similarly 10-fold, 100-fold and 1000-fold. 0.1 ml of each dilution is spread on an agar medium such as dilute glucose-asparagine (glucose, 1.0 g; asparagine, 0.05 g; dibasic potassium phosphate, 0.05 g; agar, 15 g; distilled water, 1 liter, pH 6.8 before autoclaving) or on tap water agar (technical grade agar, 15 g; tap water, 1 liter) and incubated at 28° C. for 4 to 5 weeks. Colonies are buff-colored and have filamentous margins.

In the case of the microorganisms identified as M1, the soil was a clay soil taken from a tropical garden in Aswan, Egypt. In the case of the microorganisms identified as M2 the soil was a clay soil taken from a field near Mehalla, Egypt, and in the case of M3, the soil was taken from a wheat field in El Arbaeen, Egypt.

Cultures of the microorganism prepared as described above have been deposited in the Agricultural Research Culture Collection (NRRL), International Depositary Authority, 1815 North University Street, Peoria, Ill. 61604, U.S.A., identified as Amycolata sp. LL-370-1 Accession No. NRRL 18391, LL-371-29 Accession No. NRRL 18392 and LL-37M-102, Accession No. NRRL 18393, by the assignee herein, Otisville BioPharm, Inc., P. O. Box 567, Otisville, N.Y. 10963. Access to the culture is available to the public. Some of the strains' physiological characteristics are listed in Table I.

TABLE I

| | Test Reactions of Amycolata spp. LL-37I-29, LL-37M-102 and LL-370-1 | | |
|---|---|---|---|
| | 37I-29 | 37M-102 | 370-1 |
| Degradation/ Transformation of | | | |
| Casein | − | − | − |
| Xanthine | + | − | − |
| Hypoxanthine | + | − | − |
| Tyrosine | + | + | + |
| Adenine | − | − | − |
| Production of | | | |
| Amylase | − | + | + |
| Gelatinase | + | − | − |
| Phosphatase | − | − | − |
| Nitrate Reductase | + | + | − |
| Urease | − | − | − |
| Esculinase | +. | + | + |
| Growth on/in | | | |
| 5% NaCl | − | − | − |
| Salicylate | + | + | + |
| Lysozyme Broth | − | − | − |
| Utilization | | | |
| Acetate | + | + | + |

TABLE I-continued

| | Test Reactions of Amycolata spp. LL-37I-29, LL-37M-102 and LL-370-1 | | |
|---|---|---|---|
| | 37I-29 | 37M-102 | 370-1 |
| Benzoate | − | − | − |
| Citrate | + | − | − |
| Lactate | + | + | + |
| Malate | + | − | − |
| Mucate | − | − | − |
| Oxalate | + | + | − |
| Propionate | + | + | − |
| Pyruvate | + | + | + |
| Succinate | + | + | + |
| Tartrate | + | − | − |
| Growth at | | | |
| 10° C. | − | − | − |
| 45° C. | + | − | + |
| 53° C. | − | − | − |
| Acid from | | | |
| Adonitol | + | − | + |
| Arabinose | + | + | + |
| Cellobiose | + | + | + |
| Dextrin | + | + | + |
| Dulcitol | + | − | − |
| Erythritol | + | + | + |
| Fructose | + | + | + |
| Galactose | + | + | + |
| Glucose | + | + | + |
| Glycerol | + | + | + |
| Inositol | + | + | + |
| Lactose | + | + | + |
| Maltose | + | + | + |
| Mannitol | + | + | + |
| Mannose | + | + | + |
| Melibiose | + | − | + |
| α-Me-D-Glucoside | + | − | − |
| Raffinose | + | − | + |
| Rhamnose | + | + | + |
| Salicin | + | − | − |
| Sorbitol | + | + | + |
| Sucrose | + | − | + |
| Trehalose | + | + | + |
| Xylose | + | + | + |
| β-Me-D-Xyloside | + | + | − |

[1] For methods see:
a. Gordon, R. E., D. A. Barnett, J. E. Handerhan and C. H.-N. Pang. 1974. *Nocardia coeliaca, Nocardia autotrophica*, and the nocardin strain. Int. J. Syst. Bacteriol. 24: 54–63.
b. Gordon, R. E., S. K. Mishra and D. A. Barnett, 1978. Some bits and pieces of the genus Nocardia: *N. carnea, N. vaccinii, N. transvalensis, N. orientalis* and *N. aerocolonigenes*. J. Gen. Microbiol. 104: 69–78.
c. Lechevalier, M. P. 1972. Description of a new species, *Oerskovia xanthineolytica* and emendation of *Oerskovia*, Prauser et al. Intern. J. Syst. Bacteriol. 22: 260–264.

Description of the Production, Isolation and Purification of the Active Immunological Adjuvants Amycolata spp. 37I-29, 37M-102 and 370-1 were grown at 28° C. on an agar slant medium such as Bennett's or yeast-dextrose agars (Lechevalier, M., *J. Lab. Clin. Med.* 71: 934, 1968) with storage at 4° C. The actinomycete strain to be tested was grown in shaken culture as follows: cells from an agar slant culture, one to two weeks old, were inoculated into a 250 ml Erlenmeyer flask of Bennett's or yeast-extract-dextrose broth dispensed at 50 ml/flask and shaken at 215 RPM for one week at 28° C. This growth was transferred at 5–10% to five to ten similar flasks of the same medium, and these shaken for one week to ten days under the same conditions. The cells were then transferred at 6% to 2-liter Erlenmeyer flasks containing 200 cc of the same or similar media and shaken at 195 RPM for one week. The cells were then autoclaved, collected by centrifugation and either worked up as described below or stored at −20° C. until used.

In general, the immunological adjuvants are extracted from the bacteria cells by suspending cells in physiological saline solution at room temperature in the presence or absence of an emulsifier or amphipath. Any temperature below a temperature at which the adjuvant is inactivated can be employed, but there is usually no need to use a temperature above about 28° C.

The suspensions are vigorously shaken for 18 hours with an inert water-immiscible organic solvent in which the immunological adjuvant is soluble and/or dispersible.

Hexane and similar aliphatic hydrocarbons having from four to eight carbon atoms are preferred. Solvents which can also be used include cycloaliphatic hydrocarbons such as cyclohexane, petroleum ether (b.p. 30°–40°), halogenated hydrocarbons such as methylene chloride, aliphatic alcohols such as n-butanol and chloroform/methanol (2:1). Emulsifiers such as Triton-X-100 and Brij 96 can also be used, but Tween and SDS are more effective. Hexane alone, without amphipath, was not effective in extracting the adjuvant.

On centrifuging the suspension, a number of layers form. These are separated and the adjuvant recovered from the organic solvent layer. The remaining layers that show adjuvant activity can be further purified by re-extraction with organic solvents or enzymatic action.

Based on the results illustrated in Table III and the results of the tests reported in Examples 1 to 38, a preferred embodiment of the method of preparation of active and non-toxic adjuvants is as follows:

EXAMPLE A

Fifty grams of cells, prepared as above, are suspended in 500 ml of pre-cooled (4° C.) 0.9% aqueous NaCl (physiological saline) for 10 minutes at high speed in an explosion-proof blender, 2.0 g of sodium dodecyl sulfate or 2.0 ml of Tween 80 ® added, and the whole blended for two minutes. This slurry was further treated by blending with 400 ml hexane for five minutes and the hexane-cell slurry further extracted by shaking 18 hours on a reciprocal shaker shaking at 60 strokes/minute. Following this, the mixture was separated into four phases by centrifugation at 2,500 RPM for ½ to two hours. The first (top) phase was clear, light amber-colored hexane; the second, emulsion; the third, cells; and the fourth (and bottom), the aqueous layer. The emulsion layer was collected and taken to dryness. This dry residue was extracted by grinding with several 5 ml aliquots of hexane, the extracted residue being retained and the hexane discarded. The typical residue is an off-white to beige powder. Typical yields of active material from 50 g of cells were 118.4 mg from hexane-Tween 80 ® extraction with 873 mg with SDS-hexane.

Examples 1 to 38 described adjuvants that have been prepared and evaluated with description of the methods of preparation; the results are given in Table II. These represent preferred embodiments of the invention. In these Examples, three different strains of Amycolata were used. One adjuvant (Example 1) was obtained using similar methods of extaction from the mycolate-containing microorganism *M. smegmatic ATCC*21732, which is known to possess good adjuvant activity (Adam, A. et al., *Infect. Immun.* 7: 855, 1973).

TABLE II

| Example No. | Microorganism Extract | Amphipath | Organic Solvent | Comments |
| --- | --- | --- | --- | --- |
| Control 1 | LPS | | | |
| Control 2 | MDP | | | |
| Example 1 | ML0 | Tween 80 | Hexane | |
| Example 2 | ML1 B1 | Tween 80 | Hexane | |
| Example 3 | B2 | Tween 80 | Hexane | |
| Example 4 | B3 | Tween 80 | Hexane | |
| Example 5 | B3 Fr 1 | Tween 80 | Hexane | Lyzozyme insoluble |
| Example 6 | Fr 2 | Tween 80 | Hexane | Lysozyme soluble, ether extract |
| Example 7 | Fr 3 | Tween 80 | Hexane | Lysozyme soluble, chloroform: methanol extract |
| Example 8 | Fr 4 | Tween 80 | Hexane | Lysozyme soluble, residue left after above extractions |
| Example 9 | ML1 L1 No. 1 | Tween 80 | Hexane | |
| Example 10 | No. 2 | Tween 80 | Cyclohexane | |
| Example 11 | No. 3 | Tween 80 | Petroleum ether | |
| Example 12 | No. 4 | Tween 80 | Methylene chloride | |
| Example 13 | No. 5 | Tween 80 | n-Butanol | |
| Example 14 | No. 6 | Tween 80 | Chloroform: methanol (2:1) | |
| Example 15 | ML1 L2 No. 1 | Tween 80 | Hexane | |
| Example 16 | No. 2 | Triton X 100 | Hexane | |
| Example 17 | No. 3 | Brij 96 | Hexane | |
| Example 18 | No. 4 | SDS | Hexane | |
| Example 19 | No. 5 | nil | Hexane | |
| Example 20 | ML1 L3 Fr 1a | Tween 80 | Hexane | Emulsion phase |
| Example 21 | Fr 1b | Tween 80 | Hexane | Emulsion phase extracted with hexane |
| Example 22 | Fr 1c | Tween 80 | Hexane | Hexane extract from Fr 1b |
| Example 23 | Fr 2a | SDS | Hexane | Emulsion phase |
| Example 24 | Fr 2b | SDS | Hexane | Emulsion phase extracted with hexane |
| Example 25 | Fr 2c | SDS | Hexane | Hexane extract from Fr 2b |
| Example 26 | Fr 3 | Tween 80 | n-Butanol | |
| Example 27 | Fr 4a1b | nil | Hexane | |
| Example 28 | ML2 B2 Fr 1 | Tween 80 | Hexane | Hexane phase |
| Example 29 | Fr 2 | Tween 80 | Hexane | Emulsion |
| Example 30 | ML2 B3 | Tween 80 | Hexane | |

TABLE II-continued

| Example No. | Microorganism Extract | Amphipath | Organic Solvent | Comments |
|---|---|---|---|---|
| Example 31 | ML3 B1 | Tween 80 | Hexane | |
| Example 32 | ML3 B2 Fr 1 | Tween 80 | Hexane | Hexane phase |
| Example 33 | Fr 2a | Tween 80 | Hexane | Emulsion phase |
| Example 34 | Fr 2b | Tween 80 | Hexane | Residue after hexane extraction of Fr 2a |
| Example 35 | Fr 2c | Tween 80 | Hexane | Hexane extraction from Fr 2a |
| Example 36 | ML3 B3 Fr 1 | SDS | Hexane | Emulsion phase |
| Example 37 | Fr 2 | SDS | Hexane | Hexane extraction from Fr 1 |
| Example 38 | Fr 3 | SDS | Hexane | Residue after hexane extraction of Fr 1 |

Explanations:
LPS—lipopolysaccharide purchased from Difco
MDP—muramyl dipeptide purchased from Sigma
ML0—*M. smegmatis* obtained from ATCC21732
Extracts designated as ML1 were obtained from Amycolata 37I-29; those designated ML2 from strain 37M-102; and those designated ML3 from 37M-102.
SDS—sodium dodecyl sulfate Analysis of the adjuvants prepared as shown in Table II showed that no mycolic acid-like materials were present. In contrast, similarly prepared material from *Mycobacterium smegmatis* ATCC 21732 contained 1% mycolates by weight.

The adjuvant activity of the adjuvants of Examples 1 to 38 was evaluated as follows.

It is well known that there is a direct relationship between adjuvant activity and the ability to induce non-specific proliferation of B-cells. B-cells are white blood cells occurring in the blood, spleen and other tissues that are responsible for the production and secretion of so called humoral antibodies occurring in the blood and other tissues. Good adjuvants invariably induce a proliferation of B-cells. The test used to measure the extent of this action was previously described by Bona, C. et al., *J. Exp. Med.* 148: 136, 1978.

In this test splenocytes (spleen cells) from BALB/C mice are incubated with various amounts of the adjuvants and the proliferation of cells associated with DNA synthesis is measured by the incorporation of radioactive $^3$H thymidine. The results were expressed as the mean counts per minutes (CPM) for triplicate cultures pulsed on day 2 with 1 u Ci (curie) of $^3$H-Td (tritiated thymidine). Thymidine is one of the four major nucleotides in DNA. When tritiated-i.e., containing the hydrogen radioisotope tritium-it is used as a radioactive marker in cell and tissue studies for new formation of DNA in which it is incorporated. The cultures were harvested and counted on day 3, 4 or 5. The stimulation index (S.I.) was the ratio of the experimental mean to the blank control mean in which no adjuvant was used. A S.I. of less than five was not statistically significant.

In each experiment a positive adjuvant control was also run. Lipopolysaccharide (LPS) was used for this purpose which is known to be the most potent adjuvant for B-cell proliferation as measured in this test.

The results obtained with adjuvants extracted by various procedures from Amycolata and other microorganisms together with the appropriate controls are given in Table III.

TABLE III

The Mitogenic Effect of Adjuvants on Spleen-Cell Proliferation

| Example No. | Adjuvant from Microorganism | | | Mean Counts Per Minute | Stimulation Index |
|---|---|---|---|---|---|
| Control 1 | LPS | | | 34,257 | 14.8 |
| Control 2 | MDP | | | 3,198 | 2.6 |
| Example 1 | ML0 | | | 9,560 | 4.8 |
| Example 2 | ML1 | B1 | | 48,331 | 20.5 |
| Example 3 | | B2 | | 42,065 | 18.0 |
| Example 4 | | B3 | | 7,115 | 8.1 |
| Example 5 | | B3 | Fr 1 | 21,858 | 22.8 |
| Example 6 | | | Fr 2 | 482 | 1.0 |
| Example 7 | | | Fr 3 | 1,984 | 4.9 |
| Example 8 | | | Fr 4 | 27,759 | 28.6 |
| Example 9 | ML1 | L1 | No. 1 | 7,710 | 15.2 |
| Example 10 | | | No. 2 | 11,040 | 22.8 |
| Example 11 | | | No. 3 | 3,235 | 7.4 |
| Example 12 | | | No. 4 | −173 | 0.6 |
| Example 13 | | | No. 5 | 603 | 2.2 |
| Example 14 | | | No. 6 | 183 | 1.4 |
| Example 15 | ML1 | L2 | No. 1 | 2,605 | 6.1 |
| Example 16 | | | No. 2 | −419 | 0.2 |
| Example 17 | | | No. 3 | −423 | 0.2 |
| Example 18 | | | No. 4 | 13,301 | 27.2 |
| Example 19 | | | No. 5 | 348 | 1.7 |
| Example 20 | ML1 | L3 | Fr 1a | 1,458 | 0.8 |
| Example 21 | | | Fr 1b | 15,556 | 8.8 |
| Example 22 | | | Fr 1c | 2,791 | 1.6 |
| Example 23 | | | Fr 2a | 25,413 | 14.4 |
| Example 24 | | | Fr 2b | 23,247 | 13.2 |
| Example 25 | | | Fr 2c | 1,848 | 1.1 |
| Example 26 | | | Fr 3 | 4,002 | 2.3 |
| Example 27 | | | Fr 4a1b | 2,138 | 1.2 |
| Example 28 | ML2 | B2 | Fr 1 | 4,211 | 2.7 |
| Example 29 | | | Fr 2 | 1,392 | 2.4 |
| Example 30 | ML2 | B3 | | 2,428 | 1.4 |
| Example 31 | ML3 | B1 | | 7,000 | 3.8 |
| Example 32 | ML3 | B2 | Fr 1 | 2,016 | 1.1 |
| Example 33 | | | Fr 2a | 10,522 | 6.0 |
| Example 34 | | | Fr 2b | 16,987 | 9.2 |
| Example 35 | | | Fr 2c | 1,071 | 0.6 |
| Example 36 | ML3 | B3 | Fr 1 | 21,731 | 13.2 |
| Example 37 | | | Fr 2 | 70,120 | 42.4 |
| Example 38 | | | Fr 3 | 21,300 | 12.9 |

The results indicate that the Amycolata 37I-29 strain yields adjuvants that are equal or superior to those obtained from mycolate-containing organisms. A few of the adjuvants are also more potent than LPS, the most potent adjuvant known, in tests measuring B-cell proliferation. Muramyl dipeptide (MDP), which has been recommended as an adjuvant, had only marginal activity in this test.

The action of selected adjuvants on non-specific cell proliferation was also evaluated in other strains of mice. Among these were the nu/nu BALB/C, also called "nude mice", which do not have T-cells so that the observed antibody formation is exclusively due to a B-cell response. Other mouse strains investigated were the C3H/HeJ animals which are genetically nonresponsive to the mitogenic and adjuvant effects of lipopolysaccharides. Another normal strain of mice called CBA/J has been used as an additional control.

The results are given in Table IV.

TABLE IV

| | The Mitogenic Effect of Adjuvants in Different Strains of Mice | | | | | |
|---|---|---|---|---|---|---|
| Example No. | Adjuvant from Microorganism | BALB/c Splenocytes | BALB/c Thymocytes | nu/nu BALB/c | C3H/HeJ | CBA/J |
| Control 1 | Nil | 1,766 | 78 | 2,381 | 3,153 | 2,299 |
| Control 2 | LPS | 85,112 | 250 | 196,508 | 4,450 | 36,930 |
| Example 1 | MDP | 4,520 | 120 | 12,441 | 4,994 | 11,216 |
| Example 2 | ML0 | 32,116 | 80 | 86,451 | 24,448 | 40,588 |
| Example 23 | ML1 L3 Fr 2a | 25,413 | 93 | 82,361 | 20,026 | 21,154 |
| Example 34 | ML3 B2 Fr 2b | 16,987 | 1,345 | 63,192 | 32,012 | 31,045 |

Results are expressed as the mean of counts per minute (CPM) for triplicate cultures pulsed on day 2 with 1 uCi of $^3$H—thymidine and harvested on day 3. Dose of all adjuvants is 10 ug.
nu/nu BALB/c are nude mice
C3H/HeJ are mice non-responsive to LPS The results indicate that the adjuvants of Examples 1 to 38 are normally effective in nude mice. This indicates that these adjuvants do not need the presence or assistance of T-cells to be mitogenic, and to induce a proliferative response in B-cells.

When the LPS non-responsive strain of mice C3H/HeJ was used, incubation of their lymphocytes with LPS did not induce any mitogenic or adjuvant action. The adjuvant, however, induced a mitogenic and adjuvant response of the same order of magnitude as has been produced by administration of these agents to normal mice. These results prove convincingly that the mitogenic and adjuvant action of these adjuvants is not and cannot be due to the presence of or contamination with lipopolysaccharides or related compounds. This finding is of great importance, since adjuvants containing lipopolysaccharides, because of the toxic effects of these substances, cannot be administered to humans or domestic animals.

The results obtained with splenocytes from CBA/J mice and other strains of mice indicate that the adjuvants of this invention show these effects not only in the BALB/C strain of mice but are also effective in all other strains in which they were tested.

The standard method for the evaluation of the immune response to corpuscular antigens is the Jerne technique, fully described by Anderson J. et al., *J. Exp. Med.* 145: 1520, 1977. With this technique animals, usually mice, are immunized with a corpuscular antigen such as sheep red blood cells (SRBCs). At various times after immunization lymphoid cells from the spleen (splenocytes) are mixed with agar and SRBCs that were used for immunization and added to the medium. After addition of complement, each antibody-forming cell in the agar plate starts secreting antibody that diffuses from the cell and hemolyses the SRBCs surrounding it. In this manner a plaque is formed. The number of plaques formed can be counted and indicate the number of antibody-forming cells that have been produced in response to the administration of the antigen. The antibodies revealed by this technique are of the IgM type. To detect IgG antibodies that bind weakly the complement, the addition of complement must be preceded by the addition into the agar plate of an anti-IgG serum.

With this technique it is possible to evaluate the kinetics of the immune response to corpuscular antigens and to measure not only the amount but also the kind of antibodies formed in response to immunization.

The first antibody that appears soon after the first administration of the antigen is IgM. This immunoglobulin M (M stands for macroglobulin) is important as one of the first lines of defense in the process of protection against bacterial and viral invaders. The other antibody, called immunoglobulin G or IgG, begins to appear only a few days after the administration of the antigen and is particularly important for the secondary response. The secondary response occurs when the antigen is injected for a second time and is followed by immediate rise of the serum level of IgG. IgG plays an important part in rapid killing or neutralizing bacterial or viral invaders with which the body has been previously in contact. It is the high affinity antibody that combines avidly with an invader immediately after its entry into the body. The anti-SRBC response constitutes one of the best models for measuring the immune response to bacterial and viral invaders.

The classic adjuvant that has proven most effective in this system is lipopolysaccharide (LPS), also called endotoxin, which induces a powerful response on both IgM and IgG formation. In the same series of tests we also evaluated muramyl dipeptides that recently attracted a lot of attention as a possible adjuvant and MLO, a mycolate-containing organism extracted by similar methods of extraction as the Amycolata strains described in this document.

Table V gives some of the results obtained in two experiments to give typical examples of the results that were obtained.

TABLE V

| | The Effect of Adjuvants on the Anti-SRBC Plaque-Forming Cell Response | | | |
|---|---|---|---|---|
| Example No. | Adjuvant from Microorganism | 4 days IgM | 7 days IgM | 7 days IgG |
| Exp. 1 | Nil | 21,802 | 16,130 | 7,770 |
| Control 1 | LPS | 64,840 | 29,320 | 17,180 |
| Control 2 | MDP | 25,190 | 12,260 | 6,850 |
| Example 1 | ML0 | 102,700 | 18,690 | 22,050 |
| Example 3 | ML1 B2 | 85,100 | 16,940 | 20,370 |
| Example 4 | ML1 B3 | 65,830 | 15,590 | 14,770 |
| Example 8 | ML1 B3 Fr 4 | 111,530 | 15,500 | 19,000 |
| Exp. 2 | Nil | 2,900 | 11,050 | 4,550 |
| Control 1 | LPS | 2,880 | 52,200 | 20,850 |
| Example 11 | ML1 L1 No. 3 | 4,400 | 63,360 | 17,600 |
| Example 13 | ML1 L1 No. 5 | 19,600 | 18,400 | 18,100 |
| Example 15 | ML1 L2 No. 1 | 3,840 | 18,100 | 21,900 |
| Example 18 | ML1 L2 No. 4 | 15,280 | 68,000 | 17,900 |

The potent adjuvant action of LPS is clearly evident in both Experiments. In Experiment 1 the peak level of IgM was reached after four days, whereas in Experiment 2 it took seven days to reach the peak response. In both experiments a significant elevation of immunoglobulin G was not reached until the seventh day. Several adjuvants that are the subject of this invention, such as ML1 B2, ML1 B3, ML1 L2 No. 1 and ML1 L2 No. 4, Examples 3, 4, 8, 15 and 18 were equal and usually superior in the adjuvant activity to LPS, which is generally recognized as the most active adjuvant. It will also be noted that these adjuvants are not only free from mycolic acids but also are at the same time equal or superior to an adjuvant prepared from a mycolate-containing strain (MLO).

It is well recognized that polysaccharides are much poorer immunogens than protein antigens. This has been a problem, particularly in the preparation of vaccines for the prevention of infections by *N. meningitidis*, *H. influenzae* and *S. pneumoniae*. The problem with development of these vaccines is particularly acute in infants who do not form antibodies to these vaccines during the first 18 months of their lives. It has now been determined that infants have a natural ontogenic delay in the formation of B-cell populations, responding to polysaccharide antigen TI2, and that this is the cause of the high incidence o meningitis produced by *N. meningitidis* and *H. influenzae* in infants.

The antibody formation to polysaccharide antigens can be best measured by utilizing the trinitrophenyl-Ficoll conjugate (TNP-Ficoll) as the antigenic stimulus. TNP-Ficoll is a soluble antigen which serves as prototype for all soluble polysaccharide antigens. The adjuvants of this invention were injected with TNP-Ficoll intraperitoneally to groups of five mice. After five days the antibodies to TNP-Ficoll were measured by the plaque forming cell response and the number of plaque-forming cells per spleen of animals receiving the antigen alone compared with those that received various adjuvants in addition. The technique used has been fully described by Mond, J. J. et al., *J. Exp. Med.* 158: 1401, 1983.

As a rule, 10 ug TNP-Ficoll was administered with 10 ug of the adjuvant, but in a few cases the dose of TNP-Ficoll was reduced to 1 ug, and the dose of the adjuvant increased to 100 ug.

Table VI gives some of the results obtained in three separate experiments.

TABLE VI

Enhancement of the Immune Response Induced by the Polysaccharide Antigen TI2

| Example No. | Adjuvant from Microorganism | | | Experiment 1 | Experiment 2 | Experiment 3 |
|---|---|---|---|---|---|---|
| Control 1 | Nil | | | 17,640 | 11,500 | 9,000 |
| Control 2 | MDP | | | 23,830 | 19,400 | 10,620 |
| Example 1 | ML0 | | | 29,770 | | |
| Example 2 | ML1 | B1 | | 13,040 | | |
| Example 3 | | B2 | | 24,480 | | |
| Example 4 | | B3 | | 33,467 | | |

TABLE VI-continued

Enhancement of the Immune Response Induced by the Polysaccharide Antigen TI2

| Example No. | Adjuvant from Microorganism | | | Experiment 1 | Experiment 2 | Experiment 3 |
|---|---|---|---|---|---|---|
| Example 5 | | B3 | Fr 1 | 34,275 | | |
| Example 6 | | | Fr 2 | | | 29,850 |
| Example 7 | | | Fr 3 | | | 14,940 |
| Example 8 | | | Fr 4 | 29,480 | | |
| Example 9 | ML1 | L1 | No. 1 | | | 23,880 |
| Example 10 | | | No. 2 | | | 14,850 |
| Example 11 | | | No. 3 | | | 17,850 |
| Example 12 | | | No. 4 | | | 15,540 |
| Example 13 | | | No. 5 | | | 19,260 |
| Example 14 | | | No. 6 | | | 15,780 |
| Example 15 | ML1 | L2 | No. 1 | | | 20,520 |
| Example 16 | | | No. 2 | | | 23,760 |
| Example 17 | | | No. 3 | | | 17,760 |
| Example 18 | | | No. 4 | | | 23,880 |
| Example 19 | | | No. 5 | | | 18,375 |
| Example 23 | ML1 | L3 | Fr 2a | | 28,500 | |
| Example 28 | ML2 | B2 | Fr 1 | 38,080 | | |
| Example 29 | | | Fr 2 | | | 17,440 |
| Example 31 | ML3 | B1 | | 36,530 | | |
| Example 34 | ML3 | B2 | Fr 2b | | 33,300 | |

The results indicate that many adjuvants of this invention more than double the antibody formation. This is remarkable, because no known adjuvant is capable of achieving such an increase with the poorly immunogenic polysaccharide antigens.

Keyhole limpet hemocyanin (KLH) coupled with TNP is a T-dependent protein of low immunogenicity. It is a soluble antigen that requires the presence of both B-cells and T-cells to induce an antibody response. Because of its very low immunogenic capacity, antibodies to TNP usually do not appear until a second "booster" injection has been given.

To evaluate the ability of adjuvants of this invention to increase antibody formation, groups of mice were immunized with trinitrophenyl-keyhole limpet hemocyanin conjugate (TNP-KLH) 100 $\mu$g with and without the adjuvants in graded doses from 1 $\mu$g, 10 $\mu$g and 100 $\mu$g. Control animals were treated with Freund's Complete Adjuvant or MDP 100 $\mu$g. Five weeks later all mice received the second injection of TNP-KLH 10 $\mu$g without the adjuvants and the number of antibody-forming cells determined by the plaque assay performed seven days after the second injection. The details of the technique used were described by Mond, J. J. et al, *J. Exp. Med.* 158: 1401, 1983.

The result of one of the tests is illustrated in Table VII.

TABLE VII

Anti-TNP Plaque-Forming Cell Response to Mice Immunized with TNP-KLH

| Adjuvant Used in Example No. | Concentration of Direct Anti-TNP the First Injection | IgM Indirect Anti-TNP PFC/Spleen | IgG PFC/Spleen |
|---|---|---|---|
| — | Nil | 480 ± 124 | 220 ± 73 |
| Control 1 | FCA | 3,760 ± 2,180 | 2,520 ± 1,200 |
| Control 2 | 100 $\mu$g MDP | 1,860 ± 545 | 650 ± 302 |
| | 1 $\mu$g ML1 L3 Fr 2a | 1,140 ± 199 | 980 ± 338 |
| Example 23 | 10 $\mu$g ML1 L3 Fr 2a | 640 ± 157 | 380 ± 180 |
| | 100 ML1 L3 Fr 2a | 920 ± 289 | 800 ± 336 |
| | 1 $\mu$g ML3 B2 Fr 2a | 1,220 ± 499 | 3,620 ± 2,407 |
| Example 33 | 10 $\mu$g ML3 B2 Fr 2a | 1,500 ± 286 | 780 ± 183 |
| | 100 $\mu$g ML3 B2 Fr 2a | 620 ± 156 | 1,100 ± 436 |
| | 1 $\mu$g ML3 B2 Fr 2b | 900 ± 243 | 800 ± 288 |
| Example 34 | 10 $\mu$g ML3 B2 Fr 2b | 940 ± 277 | 480 ± 120 |
| | 100 $\mu$g ML3 B2 Fr 2b | 740 ± 374 | 360 ± 175 |
| | 1 $\mu$g ML3 B2 Fr 2c | 1,180 ± 414 | 720 ± 262 |

TABLE VII-continued

Anti-TNP Plaque-Forming Cell Response to Mice Immunized with TNP-KLH

| Adjuvant Used in Example No. | Concentration of Direct Anti-TNP the First Injection | IgM Indirect Anti-TNP PFC/Spleen | IgG PFC/Spleen |
|---|---|---|---|
| Example 35 | 10 μg ML3 B2 Fr 2c | 1,040 ± 216 | 520 ± 198 |
| | 100 μg ML3 B2 Fr 2c | 1,480 ± 994 | 840 ± 314 |

Results are expressed as the mean ± SEM for 5 mice in each group. All mice received 100 μg TNP-KLH along with the adjuvant in the first injection. Five weeks later they were given the second injection and the plaque assay was performed 7 days after the second injection.

FCA caused the greatest increase in IgM as evaluated by the average number of anti-TNP-KLH plaque-forming cells. However, this increase was not statistically significant, as is evident from the large standard deviation, and occurred only in two out of five mice. It will be noted that several adjuvants of this invention caused a significant increase of both IgM and IgG antibodies to the weakly immunogenic TNP-KLH antigen.

The immune system in humans and animals can be divided into two major parts—one involving humoral immunity and the other immunocompetent cells. The preceding shows that the adjuvants of this invention strongly increase the formation of humoral antibodies. Cellular immunity is of particular importance in counteracting intracellular infections, in immunity to tumors, and in transplant rejection.

Despite the development of a multitude of complex procedures for the assessment of cellular immunity, the relatively simple test for the measurement of the delayed-type hypersensitivity remains the most accurate and reliable. In this test guinea pigs were injected into each hind foot pad with keyhole limpet hemocyanin (KLC). An antigen of low immunogenicity was given alone or in addition to adjuvants of this invention. Twenty-eight days later the animals were injected intracutaneously with KLH and the surface area of the erythema measured after challenge. A dose of purified protein derivative (PPD) obtained from M. tuberculosis was injected into a separate area of the skin at the same time. The details of the technique used were previously described by Adam et al., Proc. Nat. Acad. Sci. USA 69: 851, 1972.

The results are given in Table VIII.

TABLE VIII

Increase of Cellular Immunity of Adjuvants as Measured by the Development of Delayed-Type Hypersensitivity

| Example No. | Immunization | PPD (20 μg) | KLH (100 μg) |
|---|---|---|---|
| Control 1 | KLH/saline | 0 | 15.86 ± 5.28 |
| Control 2 | KLH/FCA | 344.16 ± 63.96 | 327.36 ± 61.02 |
| Example 23 | KLH/ML1 L3Fr2a | 0 | 63.14 ± 27.45 |
| Example 34 | KLH/ML3 B2 Fr 2b | 0 | 123.15 ± 30.79 |
| Example 35 | KLH/ML3 B2 Fr 2c | 0 | 60.32 ± 15.97 |

Animals received an injection of 1 mg KLH/adjuvant divided equally into each hind foot pad. The dose of adjuvant was 100 μg. The animals were challenged 28 days after immunization and the surface area (MM$^2$) of erythema measured 24 hours after challenge.

The results indicate that these adjuvants are able to substantially increase cellular immunity as measured by the intensity of the delayed-type hypersensitivity. All products tested were devoid of tuberculin-like activity as determined by the absence of any reaction to PPD. It is particularly remarkable that these adjuvants may increase cellular immunity when administered in aqueous solution. Other standard adjuvants such as FCA or MDP increase cellular immunity only when suspended in an oily emulsion such as Freund's Incomplete Adjuvant. The observation that these adjuvants can be administered in aqueous solution is of great importance because administration of existing adjuvants in oily emulsions results because of the presence of oil in the formation of granulomatous reactions at the site of injection which may lead to the formation of severe local reactions in the muscle such as fluctuant nodules or abscess formation. Liberation of free fatty acids from the oil in the body tissues has led to toxic reaction. It is therefore of great practical importance that the adjuvants of this invention can be administered and are effective when given in aqueous solution without the addition of any oil.

It is well known that the principal reason why adjuvants are not used in human and veterinary vaccines is their proclivity to induce adjuvant arthritis. Thus it is important to determine whether the adjuvants of this invention produce adjuvant arthritis. The technique used to determine this was described by Waksman, B. H. et al., J. Immunol. 85: 403, 1960 and Pearson, C. M., J. Chron. Dis. 16: 863, 1963. To induce adjuvant arthritis, male Sprague Dawley rats weighing 160-190 grams, receive 0.2 ml of Freund's Complete Adjuvant in the left hind foot pad. This invariably induces arthritic changes in all limbs within 21 days. Five rats received either FCA or adjuvants of this invention. The rats were examined five times weekly and the right hind limb, left fore limb and right fore limb were carefully inspected and graded for edema, erythema and mobility. Each limb was assigned a score of 1 to 4 based on the severity of the impairment—4 being the most severe and 1 being the least severe. The animals were weighed on days 0, 7, 14 and 21.

Freund's Complete Adjuvant served as a control in each experiment. Other controls used were commercially available typhoid vaccine and DPT (diphtheria, pertussis, tetanus) vaccine. Other compounds tested were Freund's Incomplete Adjuvant and MDP.

All the adjuvants of the Examples were suspended in sterile phosphate buffered saline solution pH 7.2. Freund's Complete Adjuvant and Freund's Incomplete Adjuvant and the typhoid and DPT vaccines were injected as commercially available. MDP was evaluated in Freund's Incomplete Adjuvant.

TABLE IX

Induction of Adjuvant Arthritis in Rats by Adjuvants and Vaccines

| Example No. | Adjuvant | Score day 21 | Relative Scores FCA | DPT | Typhoid |
|---|---|---|---|---|---|
| Control 1 | Freund's Complete Adjuvant | 46 | 1.0 | 2.7 | 3.3 |
| Control 2 | MDP 100 μg | 36 | 0.8 | 2.1 | 2.6 |
| Control 3 | DPT | 17 | 0.4 | 1.0 | 1.2 |

TABLE IX-continued

Induction of Adjuvant Arthritis in Rats by Adjuvants and Vaccines

| Example No. | Adjuvant | Score day 21 | Relative Scores FCA | DPT | Typhoid |
|---|---|---|---|---|---|
| Control 4 | Typhoid vaccine | 14 | 0.3 | 0.8 | 1.0 |
| Example 23 | ML1 L3 Fr 2a 1 µg | 12 | 0.3 | 0.7 | 0.9 |
|  | 10 µg | 12 | 0.3 | 0.7 | 0.9 |
|  | 100 µg | 10 | 0.2 | 0.6 | 0.7 |
| Example 33 | ML3 B2 Fr 2a 1 µg | 12 | 0.3 | 0.7 | 0.9 |
|  | 10 µg | 12 | 0.3 | 0.7 | 0.9 |
|  | 100 µg | 11 | 0.2 | 0.6 | 0.8 |
| Example 34 | ML3 B2 Fr 2b 1 µg | 12 | 0.3 | 0.7 | 0.9 |
|  | 10 µg | 12 | 0.3 | 0.7 | 0.9 |
|  | 100 µg | 10 | 0.2 | 0.6 | 0.7 |
| Example 5 | ML1 B3 Fr 1 10 µg | 14 | 0.3 | 0.8 | 1.0 |
| Example 8 | ML1 B3 Fr 4 10 µg | 11 | 0.2 | 0.6 | 0.8 |

As noted in Table IX, the adjuvants of this invention did not induce adjuvant arthritis. The scoring obtained with them in the adjuvant arthritis test was of the same order of magnitude or lower than those produced by standard, commercially available and widely used vaccines such as DPT (diphtheria, pertussis, tetanus) or typhoid vaccine which are known never to have produced arthritis in man. It is of particular interest that these adjuvants did not increase their proclivity to induce adjuvant arthritis with increasing doses, indicating the absence of adjuvant-arthritis-inducing substances in these preparations. MDP, on the other hand, as previously reported, induced marked adjuvant arthritis (Nagao and Tanaka, *Infect. Immun.* 28: 624, 1980) and confirmed that MDP can substitute for mycobacteria when used in Freund's Incomplete Adjuvant (Adam, A. and Lederer, E., *Medic. Res. Rev.* 4: 111, 1984).

Lipopolysaccharides (LPS) or endotoxins are substances isolated from gram-negative and certain other microorganisms that have many interesting biological properties. Among these is their ability to act as adjuvants, but they cannot be used for this purpose because of the many toxic manifestations they elicit, such as fever, leucopenia, increased sensitivity to catecholamines, hemorrhagic necrosis and the local and generalized Shwartzman reaction, profound vasomotor disturbances and shock (Berger, F. M., *Advances in Pharmacology* 5: 19, 1956). It is therefore of great importance that adjuvants and vaccines for human or veterinary use be free from LPS.

The Limulus Amebocyte Lysate method accurately and quantitatively determines the amount of LPS present in a sample. The test is of extreme sensitivity and will detect as little as 0.125 EU/ml, which could be called a faint trace of LPS that would be undetectable by any other method.

Table X gives the results of the tests which indicate that there are no detectable traces of LPS in adjuvants of this invention.

TABLE X

Liposaccharide Content of Adjuvants as Determined by the Limulus Amebocyte Lysate Test

| Example No. | Adjuvant | Result |
|---|---|---|
| Control 1 | LPS | Clot formation |
| Control 2 | Negative control | Less than 0.125 EU/ml |
| Example 23 | ML1 L3 Fr 2a | Less than 0.125 EU/ml |
| Example 33 | ML3 B2 Fr 2a | Less than 0.125 EU/ml |
| Example 34 | ML3 B2 Fr 2b | Less than 0.125 EU/ml |
| Control | Typhoid vaccine | Less than 0.125 EU/ml |

The complete freedom from LPS in the adjuvants of this invention is further confirmed by the observation that our compounds show marked adjuvant action in mice of the C3H/HeJ strain that is unresponsive to LPS.

It is known that certain substances, such as LPS, produce polyclonal B-cell activation—i.e., produce plaque-forming cells to an antigen, such as SRBCs—by themselves in the absence of the antigenic stimulus. If a product possesses a high polyclonal B-cell activating effect, it is difficult to evaluate the anti-SRBC immune-enhancing effect because one cannot be sure whether the increased number of plaque-forming cells is due to a true enhancement of the specific immune response or to a non-specific polyclonal B-cell activation.

Table XI gives data for a number of adjuvants of the invention.

TABLE XI

Polyclonal B-cell Activation by Adjuvants

| Example No. | Adjuvant | SRBC | Stimulation Index |
|---|---|---|---|
| Example 28 | ML2 Fr 1 | none | 1.1 |
| Example 29 | ML2 Fr 2 | none | 0.8 |
| Example 30 | ML3 | none | 0.4 |
| Example 28 | ML2 Fr 1 | 10⁷ | 32.0 |
| Example 29 | ML2 Fr 2 | 10⁷ | 28.7 |
| Example 31 | ML3 | 10⁷ | 73.3 |

As is apparent from Table XI, adjuvants of this invention when given alone do not increase the number of plaque-forming cells, but do so very strongly when given together with SRBCs.

The immunological adjuvants in accordance with the invention can be administered to animals as a class, including man, and both large and small animals, by any conventional administration procedure, including, for example, oral administration, transdermal administration, transnasal administration, sublingual administration, rectal administration, and parenteral administration.

The immunological adjuvants can be administered per se, but are usually given together with one or more of the specific antigens. Specific antigens that can be used for this purpose include:

*Bacillus anthracis*
*Bordetella pertussis*
*Brucella abortus*
*Brucella melitensis*
*Brucella suis*
Cholera toxin
Cholera toxin beta subunit
Cholera toxin alpha subunit
Cholera vaccine
*Clost. botulinum* alpha and beta toxins
*Clost. Novyi* toxoid
*Clost. oedematiens* toxoid
*Clost. perfringens*
*Clost. perfringens* toxoid
*Clost. tetani*
*Coryn. diphtheriae*
*Coryn. equi*
*Coryn. parvum*
Diphtheria toxin
Diphtheria toxoid
*Esch. coli*
*Francisella tularensis*
*Hemophilus influenzae*
*Hemophilus influenzae* group b antigen
*Legionella*
*Legionella pneumophila* group 1-6 antigens Lepromin
Leptospira antigens
*Kelbsiella pneumoniae*
*Pseudomonas aeruginosa*
*Salm. abortus* equi
*Serr. marcescens*
*Shig. flexneri*
*Shig. dysenteriae* group A, A1, B, C, C1, C2, D antigens
Vibr. Cholerae
*Yersinia enterocolitica*
Listeria
Micrococcus
Mycobacteria
*M. leprae* glycolipids I, II and III
*M. vaccae*
Mycoplasma
*Mycoplasma pneumoniae* CF antigen
*Neisseria meningitidis*
*Neisseria meningitidis* polysaccharide vaccine groups A, C, Y, W-135
Pertussis vaccine
*B. Pertussis* lymphocytosis-promoting factor
Pertussis toxin (islet-activating protein)
*N. gonorrhoeae*
*N. gonorrhoeae* pilus protein
*N. gonorrhoeae* glycoprotein
*N. gonorrhoeae* principal outer membrane protein
Chlamydia
Protein A
Proteus
*Pseudomonas aeruginosa*
*Reiter treponema* antigen
Salm. N antigens a, b, c, d, eh, g, i
Salm. O antigens A through I+Vi
*Salm. enteritidis* H antigen
*Salm. enteritidis* O antigen
*Salm. paratyphi* H antigens a, b, c
*Salm. paratyphi* O antigens A, B. C
*Salm. typhi* H antigen
*Salm. typhi* O antigen
*Salm. typhi* Vi antigen
*Salm. typhi* vaccine
*Salm. typhimurium*
Staph. alpha toxin
*Staph. enterotoxins* A, B, C1, C2, D, E
Staph. protein A
Strep. antigens groups A, B, C, D, F, G
*Strep. faecolis*
*Strep. pneumoniae* polysaccharide antigens—14 types
Streptolysin O
*Swine crysipelas* vaccine
Syphilis antigens FTA-ABS sorbent, RPR, VDRL
*T. pallidum*
Tetanus toxoid
Typhoid vaccine
Mycoviruses
Adenoviruses types 1-35+7a
Adenoviruses human group CF antigen
Adenoviruses pig
Avian leukosis—sarcoma—22 strains
Avian myeloblastosis
Avian reticuloendotheliosis—4 strains
Avian tumor viruses
Bovine leutemia (BLV-FLK purified)
Bovine papilloma
Bovine polular stomatitis
Bovine parvo
Bovine resp. syncytial
*Bovine biral diarrhoea*
Burkitt's lymphoma
Canarypox
Canine distemper
Canine parainfluenza
Colorado tick fever
Corona OC-43 and 229E
Coronaviruses from cat, chicken, dog, human, mouse, pig, rat
Coxsackie A1 through A20
Coxsackie B1 to B6
Creuzfeld-Jacob virus
Cytomegolo virus and CF antigen
Dengue types 1-4
Duck hepatitis
ECHO virus including types 1-9 and 11-33
EMBU
Encephalitis virus, California, Eastern, equine, Japanese B, Russian spring-summer, St. Louis, Venezuela equine, Western equine
Enterovirus types 68-71
Epstein-Barr virus and copsid Ag, early AgD, AgR, nuclear Ag, DNA
Equine arteritis
Equine herpes, all types
Equine infectious anemia
Feline leukemia
Feline panleukopenia
Feline picornoviruses—8 strains
Fowlpox—5 strains
GD-VIII virus (Theiler)
Goose hepatitis
Hepatitis A
Hepatitis B vaccine and surg Ag (ad), (adr), (adw), (ay), (ayw)
Herpes saimiri
Herpes simplex 1 and 2 vaccines and CF Ag, MS
Hog cholera
Influenza (avian)
Influenza A—11 strains
Influenza A vaccine
Influenza A CF Ag and A1CH1/2/68
Influenza A equine 1 and 2
Influenza A (FM-1/47)
Influenza A (Japan/170/62)
Influenza A (Japan/305/57)
Influenza A (PR-8/34)
Influenza A (Swine/1976/31)
Influenza A (Taiwan/1/64)
Influenza A (USSR/90/77)
Influenza A (Victoria/3/75) HA Ag
Influenza A (WS/33)
Influenza A1—Various strains
Influenza A2—various strains
Influenza B—various strains
Influenza A vaccine
Influenza B vaccine
Influenza B (Great Lakes/1739/54)
Influenza B (Hong Kong/8/73) HA Ag
Influenza B (Lee/40)
Influenza B (Maryland/1/59)
Influenza B (Mass/3/66) HA Ag
Influenza B (Singapore/3/64)
Influenza B (Taiwan/2/62)
Influenza B (Taylor/1233/47)
Influenza C
Kuru virus
K virus LDH virus
Lymphocytic choriomeningitis
Marek's disease
Measles vaccine
Measles CF and HA Ags
MMTV
Monkeypox
Mouse hepatitis
Mumps vaccine
Mumps CF ag, HA Ag
Murine leukemias
Murine sarcomas
Mycoviruses—38 strains
Newcastle disease vaccine
Oncogenic viruses
Parainfluenza 1–5, 1 CF and HA Ags
Picorna virus
Polio virus vaccine—strains 1, 2 and 3
Polyoma vaccine
Rabbit fibroma
Rabbit myxoma
Rabbitpox
Rabbies—6 strains
Rabbies vaccine
Raccoonpox
Rauscher leukemia virus
Reovirus from birds, cow, man, monkey
Resp. syncytial vaccine and CF antigen
Retroviruses—14 strains
Retrovirus vaccine
Rotavirus
Rous sarcoma virus
Rubella vaccine
Rubella CF and HA antigens
Semliki forest virus
Sendai virus
Simian adenovirus hyper 1-26
Simian cytomegolovirus
Simian foamy
Simian herpes
Simian oncorna
Simian paramyxo
Simian picorna
Simianpox
Simian reo
Simian rota
Simian sarcoma
Sindbis virus
Smallpox vaccine
Swinepox
Vaccinia virus
Varicella vaccine
Varicella Zoster vaccine
Vesicular stomatitis virus
West Nile virus
Yaba tumor poxvirus
Yellow fever vaccine
Chlamydia CF Ag
Bovine encephalomyelitis chlamydiae
Inclusion conjunctivitis chlamydiae
Lymphogranuloma venereum
Meningopneumonitis
Ornithosis
Ovine chlamydial abortion
Ovine polyarthritis
Psittacosis
Sporadic bovine encephalomyelitis
Trachoma

*Coxiella burneti*
*Rickettsia akari*
*Rickettsia canada*
*Rickettsia montana*
*Rickettsia prowazeki*
*Rickettsia rickettsu*
*Rickettsia tsutsugamushi*
Tha tick typhus
Fungus extracts
Aspergillus (various strains)
Blastomyces
*Candida albicans*
Coccidioides
Histophasma
Micropolyspora
Neurospora (various strains)
Saccharomonospora
Saccharomyces
Trichophyton
Algae
Acanthamoeba
Amoebae
Babesia
Chlamydomonas
Crithidia
Entamoeba (various strains)
Herpetomonas
Hypotrichononas
Leishmania (various strains)
Leptomonas
Naegleria
Phytomonas
Plasmodium (various strains)
Rhizopods
Toxoplasma gondii
Trichomonas (various strains)
Trypanosoma (various strains)
*Echinococcus granulosis*
*Fasciola hepatica*
*Hymenolepis diminuta*
*Schistosoma hematobiam*
Schistosoma Japonicum
*Schistosoma mansoni*
Ascaris (various strains)
Nematodes (various strains)
*Trichinella spiralis*

All of these are commercially available and are listed in Linscott's Directory of Immunological and Biological Reagents 3rd Edition 1984–1985. These include vaccines, intact microorganisms such as viruses, chlamydiae, rickettsiae, bacteria and bacterial antigens, fungi, protoza, algae and slime molds, platyhelminthes, nemathelminthes, annelida, anthropoda, molusca and others, as well as extracts, purified fractions and subunits.

The specific antigen administered with the adjuvant may be the killed or inactivated intact microorganism, an extract prepared from the microorganisms or a small portion of the microorganism responsible for the induction of protective antibodies (the subunit). The specific antigen in any of the above-mentioned forms may be physically mixed with the adjuvant or chemically coupled or covalently linked with the help of coupling reagents in accordance with standard procedures as described by K. Lynn Cates et al., *Infect. Immun.* 48:183, 1985 or Chiayung Chu et al., *Infect. Immun.* 40:245, 1983. The antigen may be used in its native form or chemically attached to a protein or fatty acid carrier.

The immunological adjuvant administered jointly with one or several of the specific antigens in a manner mentioned in the previous paragraph is usually given in association with a pharmaceutically acceptable diluent or carrier. The invention accordingly also provides a pharmaceutical composition in dosage unit form comprising from 0.001 to about 50 mg of immunological adjuvant, per dosage unit, together with a pharmaceutically acceptable nontoxic inert carrier or diluent therefor.

The immunological adjuvant can be administered to the animal in an amount sufficient to increase the immune response of antigens, and will depend upon the species of animal, and the weight of the animal. For example, in human administration, a dosage of immunological adjuvant within the range from about 0.001 mg/kg to about 50 mg/kg per day is therapeutically effective. In the treatment of lower test animals, a similar dosage range is therapeutic. The upper limit of dosage is that imposed by toxic side effects, and can be determined by trial and error for the animal to be treated, including humans.

To facilitate administration, the immunological adjuvant can be provided in composition form, and preferably in dosage unit form. While the compound can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the immunological adjuvant. Exemplary diluents and carriers include lactose, dextrose, sucrose, sorbitol, mannitol, starches, gum acacia, calcium phosphate, mineral oil, cocoa butter, oil of theobroma, alginates, tragacanth, gelatin syrup, methyl cellulose, polyoxyethylene sorbitan monolaurate, methyl- and propylhydroxybenzoate, talc or magnesium stearate.

For convenience in handling, the immunological adjuvant and carrier or diluent can be enclosed or encapsulated in a capsule, sachet, cachet, gelatin, paper or other container, especially when intended for use in dosage unit form. The dosage units can for example take the form of tablets, capsules, suppositories or cachets.

The following Examples illustrate various forms of dosage units in which the immunological adjuvant can be prepared:

EXAMPLE I

| Tablet formulation | Mg/tablet |
|---|---|
| Immunological adjuvant | 15 |
| Lactose | 86 |
| Corn starch (dried) | 45.5 |
| Gelatin | 2.5 |
| Magnesium stearate | 1.0 |

The immunological adjuvant is powdered and passed through a mesh sieve and well mixed with the lactose and 30 mg of the corn starch, both passed through a sieve.

The mixed powders are massed with a warm gelatin solution, prepared by stirring the gelatin in water and heating to form a 10% w/w solution. The mass is granulated by passing through a sieve, and the moist granules dried at 40° C.

The dried granules are regranulated by passing through a sieve and the balance of the starch and the magnesium stearate is added and thoroughly mixed.

The granules are compressed to produce tablets each weighing 150 mg.

EXAMPLE II

| Tablet formulation | Mg/tablet |
|---|---|
| Immunological adjuvant | 100 |
| Lactose | 39 |
| Corn starch (dried) | 80 |
| Gelatin | 4.0 |
| Magnesium stearate | 2.0 |

The method of preparation is identical with that of Example I except that 60 mg of starch is used in the granulation process and 20 mg during tabletting.

EXAMPLE III

| Capsule formulation | Mg/capsule |
|---|---|
| Immunological adjuvant | 250 |
| Lactose | 150 |

The immunological adjuvant and lactose are passed through a sieve and the powders well mixed together before filling into hard gelatin capsules of suitable size, so that each capsule contains 400 mg of mixed powders.

EXAMPLE IV

| Suppositories | Mg/suppository |
|---|---|
| Immunological adjuvant | 50 |
| Oil of Theobroma | 950 |

The immunological adjuvant is powdered and passed through a sieve and triturated with molten oil of theobroma at 45° C. to form a smooth suspension.

The mixture is well stirred and poured into molds, each of nominal 1 g capacity, to produce suppositories.

EXAMPLE V

| Cachets | Mg/cachet |
|---|---|
| Immunological adjuvant | 100 |
| Lactose | 400 |

The immunological adjuvant is passed through a mesh sieve, mixed with lactose previously sieved and fitted into cachets of suitable size so that each contains 500 mg.

EXAMPLE VI

| Intramuscular injection (sterile suspension in aqueous vehicle) | Mg |
|---|---|
| Immunological adjuvant | 10 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

EXAMPLE VII

| Intraperitoneal intraveneous or subcutaneous injection (sterile solution in aqueous carrier system) | Mg |
|---|---|
| Immunological adjuvant | 15 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

Broadly speaking, the preparation of new vaccines has three aims:

1. To prepare vaccines that would protect against diseases against which protection is not possible today.

2. To purify existing vaccines so that they would not induce adverse reactions or unpleasant side effects.

3. To produce vaccines more cheaply so that the existing vaccines could be made available to more people.

These three aims are attainable with the use of non-toxic adjuvants.

It is now known that only a small portion of the pathogenic microorganism represents an antigenic entity against which, under appropriate conditions, protective antibodies are produced. These small portions are often called subunits and represent specific segments of the peptide chain which when administered together with a suitable adjuvant induce specific protective antibodies. The use of subunit vaccines will make it possible to eliminate from existing vaccines that part of the molecule that is responsible for the side effects and adverse reactions that vaccines may induce. Other vaccines, such as hepatitis B, are very expensive. An addition of adjuvant to such a vaccine would permit the utilization of much smaller amounts of the specific antigen and thus substantially decrease the cost of the vaccine.

Having regard to the foregoing disclosure, the following is claimed as the inventive and patentable embodiments thereof:

1. A process for preparing an immunological adjuvant that when administered to animals increases the immune response to antigens, and that is substantially free from mycolic acids, mycolic acid esters, and lipopolysaccharides, which comprises suspending Amycolata bacteria cells in aqueous saline solution; extracting the cells with an inert organic solvent in which the immunological adjuvant is soluble or dispersible; separating the organic solvent solution from the bacteria cells and the aqueous saline solution; and recovering immunological adjuvant.

2. A process according to claim 1 in which the extraction is carried out in the presence of an emulsifying agent.

3. A process according to claim 2 in which the emulsifying agent is an organic surfactant.

4. A process according to claim 3 in which the organic surfactant is sodium dodecyl sulphate.

5. A process according to claim 1 in which the organic solvent is an aliphatic hydrocarbon having from about four to about eight carbon atoms.

6. A process according to claim 5 in which the aliphatic hydrocarbon is hexane.

7. A process according to claim 1 in which the organic solvent is a cycloaliphatic hydrocarbon.

8. An immunological adjuvant substantially free from mycolic acids, mycolic acid esters, and lipopolysaccharides, and capable of increasing the immune response of an antigen upon administration to an animal body, prepared in accordance with the process of claim 1.

9. An immunological adjuvant according to claim 8, in which the extraction is carried out in the presence of an emulsifying agent.

10. An immunological adjuvant according to claim 9, in which the emulsifying agent is an organic surfactant.

11. An immunological adjuvant according to claim 10, in which the organic surfactant is sodium dodecyl sulphate.

12. An immunological adjuvant according to claim 8, in which the organic solvent is an aliphatic hydrocarbon having from about four to about eight carbon atoms.

13. An immunological adjuvant according to claim 12, in which the aliphatic hydrocarbon is hexane.

14. An immunological adjuvant according to claim 8, in which the organic solvent is a cycloaliphatic hydrocarbon.

15. A process for increasing the immune response of antigens which in animals induce the formation of antibodies, which comprises administering to the animal an immunological adjuvant prepared according to the process of claim 1, and an antigen.

16. A process according to claim 15 in which both the immunological adjuvant and the antigen are administered together.

17. A process according to claim 15 in which both the immunological adjuvant and the antigen are administered separately.

18. A process according to claim 15 in which the immunological adjuvant is administered parenterally.

19. A pharmaceutical composition for increasing the immune response of antigens which in the animal body induce the formation of antibodies, comprising an immunological adjuvant prepared according to the process of claim 1, and a pharmaceutically-acceptable non-toxic carrier or diluent.

20. A pharmaceutical composition according to claim 19 which also comprises an antigen.

21. A pharmaceutical composition according to claim 19 in dosage unit form.

22. A pharmaceutical composition according to claim 21 which also includes an antigen.

* * * * *